(12) United States Patent
Ehrenfreund et al.

(10) Patent No.: US 7,951,752 B2
(45) Date of Patent: May 31, 2011

(54) O-CYCLOPROPYL-CARBOXANILIDES AND THEIR USE AS FUNGICIDES

(75) Inventors: Josef Ehrenfreund, Basel (CH); Hans Tobler, Basel (CH); Harald Walter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 687 days.

(21) Appl. No.: 10/506,918

(22) PCT Filed: Feb. 21, 2003

(86) PCT No.: PCT/IB03/00687
§ 371 (c)(1), (2), (4) Date: Apr. 28, 2005

(87) PCT Pub. No.: WO03/074491
PCT Pub. Date: Sep. 12, 2003

(65) Prior Publication Data
US 2005/0221989 A1    Oct. 6, 2005

(30) Foreign Application Priority Data

Mar. 5, 2002 (GB) .................................. 0205127.4
Jan. 13, 2003 (GB) .................................. 0300705.1

(51) Int. Cl.
*A01N 25/00* (2006.01)
*C07D 43/00* (2006.01)

(52) U.S. Cl. ...................... 504/239; 548/374.1; 548/537

(58) Field of Classification Search .................. 548/205, 548/374.1, 537; 514/371; 504/239
See application file for complete search history.

(56) References Cited

U.S. PATENT DOCUMENTS

| | | | |
|---|---|---|---|
| 5,438,070 A | 8/1995 | Eicken et al. |
| 5,480,897 A | 1/1996 | Eicken et al. |
| 5,498,624 A | 3/1996 | McLoughlin et al. |

FOREIGN PATENT DOCUMENTS

| | | |
|---|---|---|
| EP | 0545099 | 6/1993 |
| JP | 02129171 | 5/1990 |
| WO | 0153259 | 7/2001 |
| WO | WO0153259 | 7/2001 |

OTHER PUBLICATIONS

Database WPI; Section Ch, Week 199026; Derwent Publications Ltd., London, GB; AN 1990-196872.

*Primary Examiner* — Sabiha Qazi
(74) *Attorney, Agent, or Firm* — William F. Mulholland, II

(57) ABSTRACT

A compound of formula (I): F1 Het is a 5- or 6-membered heterocyclic ring containing one to three heteroatoms, each independently selected from oxygen, nitrogen and sulphur, the ring being substituted by groups $R^4$, $R^5$ and $R^6$; $R^1$ is hydrogen or halo; $R^2$ is hydrogen or halo; $R^3$ is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; and $R^4$, $R^5$ and $R^6$ are, independently, selected from hydrogen, halo, cyano, nitro, $C_{1-4}$ haloalkyl, $C_{1-4}$ alkoxyl ($C_{(1-4)}$ alkoxyl ($C_{1-4}$) alkyl and $C_{1-4}$ haloalkoxy ($C_{1-4}$) alkyl, provided that at least one of $R^4$, $R^5$ and $R^6$ is not hydrogen. The compounds of formula (I) have plant-protective properties and are suitable for protecting plants against infestations by phytopathogenic microorganisms.

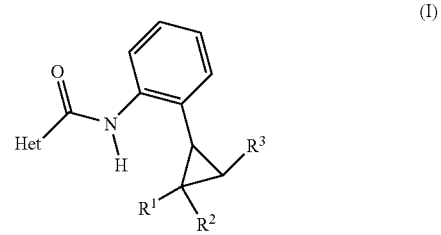

(I)

3 Claims, No Drawings

O-CYCLOPROPYL-CARBOXANILIDES AND THEIR USE AS FUNGICIDES

This is a national stage application under 35 U.S.C. §371 of International Application No. PCT/IB03/00687, filed on Feb. 21, 2003, which is entitled to the benefit of Great Britain Application No. 0205127.4, filed on Mar. 5, 2002 and Great Britain Application No. 0300705.1, filed on Jan. 13, 2003, which are incorporated by reference in their entireties.

The present invention relates to novel ortho-substituted-cyclopropyl-azol-carboxamides which have microbiocidal activity, in particular fungicidal activity. The invention also relates to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

EP0545099A2, JP06220035 and JP02129171 disclose certain ortho-unsubstituted-cyclopropyl-azol-carboxamides.

The present invention provides a compound of formula (I):

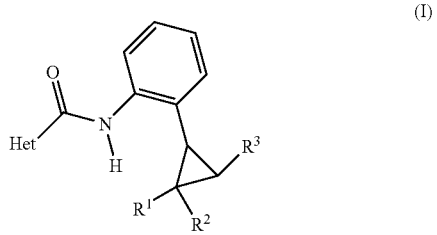

(I)

Het is a 5- or 6-membered heterocyclic ring containing one to three heteroatoms, each independently selected from oxygen, nitrogen and sulphur, the ring being substituted by groups $R^4$, $R^5$ and $R^6$; $R^1$ is hydrogen or halo; $R^2$ is hydrogen or halo; $R^3$ is optionally substituted $C_{2-12}$ alkyl, optionally substituted $C_{2-12}$ alkenyl, optionally substituted $C_{2-12}$ alkynyl, optionally substituted $C_{3-12}$ cycloalkyl, optionally substituted phenyl or optionally substituted heterocyclyl; and $R^4$, $R^5$ and $R^6$ are, independently, selected from hydrogen, halo, cyano, nitro, $Cl_{1-4}$ alkyl, $C_{1-4}$ haloalkyl, $C_{1-4}$ alkoxy($C_{1-4}$)alkyl and $C_{1-4}$ haloalkoxy($C_{1-4}$)alkyl, provided that at least one of $R^4$, $R^5$ and $R^6$ is not hydrogen.

Halo is fluoro, chloro or bromo.

Each alkyl moiety is a straight or branched chain and is, for example, methyl, ethyl, n-propyl, n-butyl, n-pentyl, n-hexyl, iso-propyl, n-butyl, sec-butyl, iso-butyl, tert-butyl or neopentyl.

When present, each optional substituent on an alkyl moiety is, independently, selected from halo, hydroxy, cyano, $C_{1-4}$alkoxyC(=O), formyl, nitro, $C_{1-4}$ alkoxy, $C_{1-4}$ haloalkoxy, $C_{1-4}$ alkylthio, $C_{1-4}$ haloalkylthio, HC(OR')=N and R'R"NN=C(H); where R' and R" are, independently, hydrogen or $C_{1-4}$ alkyl.

Alkenyl and alkynyl moieties can be in the form of straight or branched chains. The alkenyl moieties, where appropriate, can be of either the (E)- or (Z)-configuration. Examples are vinyl, allyl and propargyl.

When present, each optional substituent on alkenyl or on alkynyl is, independently, selected from those optional substituents given above for an alkyl moiety.

Cycloalkyl includes cyclopropyl, cyclobutyl, cyclopentyl and cyclohexyl.

When present, each optional substituent on cycloalkyl is, independently, selected from $C_{1-3}$ alkyl and those optional substituents given above for an alkyl moiety.

The term heterocyclyl refers to a non-aromatic or aromatic ring containing up to 10 atoms including one or more (preferably one or two) heteroatoms selected, each independently, from O, S and N. Examples of such rings include 1,3-dioxolanyl, tetrahydrofuranyl, morpholinyl, thienyl and furyl.

When present, each optional substituent on phenyl or on heterocyclyl is, independently, selected from $C_{1-6}$ alkyl and those optional substituents given above for an alkyl moiety. When present, there are up to four optional substituents on phenyl, each independently selected.

When present, each optional substituent on an alkyl moiety is, independently, selected from the preferred list of halo, hydroxy, methoxy, trifluoromethoxy, difluoromethoxy, cyano and nitro.

When present, each optional substituent on alkenyl or on alkynyl is, independently, selected from the preferred list of halo and cyano.

When present, each optional substituent on cycloalkyl is, independently, selected from the preferred list of methyl, ethyl, trifluoromethyl, methoxy, trifluoromethoxy and cyano.

When present, each optional substituent on phenyl or on a heterocyclyl group is, independently, selected from the preferred list of halo, hydroxy, methoxy, trifluoromethoxy, difluoromethoxy and cyano.

It is preferred that Het is pyrrolyl, pyrazolyl, thiazolyl, pyridinyl, pyrimidinyl, thiophenyl, furyl, isothiazolyl or isoxazolyl (more preferably pyrrolyl, pyrazolyl or thiazolyl), each being substituted by groups $R^4$, $R^5$ and $R^6$.

Preferably $R^1$ and $R^2$ are, independently, hydrogen or fluoro.

Preferably $R^3$ is $C_{2-6}$ alkyl, optionally substituted $C_{3-8}$ cycloalkyl, phenyl, thienyl or furyl.

Preferably $R^4$, $R^5$ and $R^6$ are, independently, selected from hydrogen, halogen, $C_{1-4}$ alkyl, $C_{1-4}$ haloalkyl and $C_{1-4}$ alkoxy ($C_{1-4}$)alkyl; provided that at least one of $R^4$, $R^5$ and $R^6$ is not hydrogen. More preferably $R^4$, $R^5$ and $R^6$ are, independently, selected from hydrogen, halogen, methyl, $C_{1-2}$ haloalkyl and methoxymethyl; provided that at least one of $R^4$, $R^5$ and $R^6$ is not hydrogen.

Compounds of formula (II):

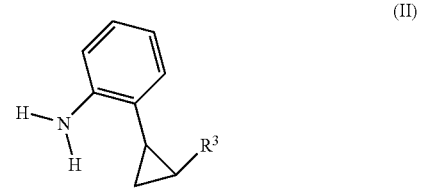

(II)

where $R^3$ is as defined above for a compound of formula (I), are also novel and are useful as intermediates in the preparation of compounds of formula (I).

Therefore, in another aspect the present invention provides a compound of formula (II) where $R^3$ is as defined above for a compound of formula (I).

The compounds of formula (I) and of formula (II) may exist as different geometric or optical isomers or in different tautomeric forms. This invention covers all such isomers and tautomers and mixtures thereof in all proportions as well as isotopic forms such as deuterated compounds.

The compounds in Tables 1 to 6 below illustrate compounds of the invention.

Table 1 provides 22 compounds of formula (II) wherein $R^3$ is as defined in Table 1.

TABLE 1

| Compound Number | $R^3$ |
|---|---|
| 1.1 | $CH_2CH_3$ |
| 1.2 | $CH_2CH_2CH_3$ |
| 1.3 | $CH(CH_3)_2$ |
| 1.4 | $CH_2CH_2CH_2CH_3$ |
| 1.5 | $CH_2CH(CH_3)_2$ |
| 1.6 | $C(CH_3)_3$ |
| 1.7 | $CH_2CH_2CH_2CH_2CH_3$ |
| 1.8 | $CH_2CH_2CH(CH_3)_2$ |
| 1.9 | $CH_2CH_2CH(CH_3)_2$ |
| 1.10 | cyclopropyl |
| 1.11 | cyclobutyl |
| 1.12 | cyclopentyl |
| 1.13 | cyclohexyl |
| 1.14 | cycloheptyl |
| 1.15 | cyclooctyl |
| 1.16 | phenyl |
| 1.17 | p-Cl-phenyl |
| 1.18 | p-F-phenyl |
| 1.19 | p-Br-phenyl |
| 1.20 | thienyl |
| 1.21 | furyl |
| 1.22 | α-methylcyclopropyl |

Table X represents Table 2 (when X is 2) and represents Table 3 (when X is 3).

TABLE X

| Compound Number | $R^1$ | $R^2$ | $R^3$ | $R^4$ | $R^5$ | $R^6$ |
|---|---|---|---|---|---|---|
| X.1 | H | H | $CH_2CH_3$ | $CF_3$ | $CH_3$ | H |
| X.2 | H | H | $CH_2CH_3$ | $CF_3$ | $CH_2OCH_3$ | H |
| X.3 | H | H | $CH_2CH_2CH_3$ | $CF_3$ | $CH_3$ | H |
| X.4 | H | H | $CH_2CH_2CH_3$ | $CF_2H$ | $CH_3$ | H |
| X.5 | H | H | $CH(CH_3)_2$ | $CF_3$ | $CH_3$ | H |
| X.6 | H | H | $CH(CH_3)_2$ | $CF_2H$ | $CH_3$ | H |
| X.7 | H | H | $CH(CH_3)_2$ | $CFH_2$ | $CH_3$ | H |
| X.8 | H | H | $CH(CH_3)_2$ | $CH_3$ | $CH_3$ | Cl |
| X.9 | H | H | $CH(CH_3)_2$ | $CH_3$ | $CH_2CH_3$ | Cl |
| X.10 | H | H | $CH(CH_3)_2$ | $CH_3$ | $CH_3$ | F |
| X.11 | H | H | $CH(CH_3)_2$ | $CH_3$ | $CH_2CH_3$ | F |
| X.12 | H | H | $CH(CH_3)_2$ | $CF_2Cl$ | $CH_3$ | F |
| X.13 | H | H | $CH_2CH_2CH_2CH_3$ | $CF_3$ | $CH_3$ | H |
| X.14 | H | H | $CH_2CH_2CH_2CH_3$ | $CF_2H$ | $CH_3$ | H |
| X.15 | H | H | $CH_2CH_2CH_2CH_3$ | $CH_3$ | $CH_3$ | F |
| X.16 | H | H | $CH_2CH_2CH_2CH_3$ | $CH_3$ | $CH_3$ | Cl |
| X.17 | H | H | $CH_2CH(CH_3)_2$ | $CF_3$ | $CH_3$ | H |
| X.18 | H | H | $CH_2CH(CH_3)_2$ | $CF_2H$ | $CH_3$ | H |
| X.19 | H | H | $CH_2CH(CH_3)_2$ | $CFH_2$ | $CH_3$ | H |
| X.20 | H | H | $CH_2CH(CH_3)_2$ | $CF_3$ | $CH_2OCH_3$ | H |
| X.21 | H | H | $CH_2CH(CH_3)_2$ | $CH_3$ | $CH_3$ | F |
| X.22 | H | H | $CH_2CH(CH_3)_2$ | $CH_3$ | $CH_3$ | Cl |
| X.23 | H | H | $C(CH_3)_3$ | $CF_3$ | $CH_3$ | H |
| X.24 | H | H | $C(CH_3)_3$ | $CF_2H$ | $CH_3$ | H |
| X.25 | H | H | $C(CH_3)_3$ | $CF_2H$ | $CH_3$ | H |
| X.26 | H | H | $C(CH_3)_3$ | $CH_3$ | $CH_3$ | F |
| X.27 | H | H | $C(CH_3)_3$ | $CH_3$ | $CH_3$ | Cl |
| X.28 | H | H | $C(CH_3)_3$ | $CF_2Cl$ | $CH_3$ | H |
| X.29 | H | H | $CH_2CH_2CH_2CH_2CH_3$ | $CF_3$ | $CH_3$ | H |
| X.30 | H | H | $CH_2CH_2CH(CH_3)_2$ | $CF_3$ | $CH_3$ | H |
| X.31 | H | H | $CH_2CH_2CH(CH_3)_2$ | $CF_2H$ | $CH_3$ | H |
| X.32 | H | H | $CH_2CH_2CH_2CH_2CH_3$ | $CF_3$ | $CH_3$ | H |
| X.33 | H | H | cyclopropyl | $CF_3$ | $CH_3$ | H |
| X.34 | H | H | cyclopropyl | $CF_2H$ | $CH_3$ | H |
| X.35 | H | H | cyclopropyl | $CH_3$ | $CH_3$ | F |
| X.36 | H | H | cyclopropyl | $CH_3$ | $CH_3$ | Cl |
| X.37 | H | H | cyclobutyl | $CF_3$ | $CH_3$ | H |
| X.38 | H | H | cyclobutyl | $CF_2H$ | $CH_3$ | H |
| X.39 | H | H | cyclopentyl | $CF_3$ | $CH_3$ | H |
| X.40 | H | H | cyclopentyl | $CF_2H$ | $CH_3$ | H |
| X.41 | H | H | cyclopentyl | $CFH_2$ | $CH_3$ | H |
| X.42 | H | H | cyclopentyl | $CF_2Cl$ | $CH_3$ | H |
| X.43 | H | H | cyclopentyl | $CH_3$ | $CH_3$ | F |
| X.44 | H | H | cyclopentyl | $CH_3$ | $CH_3$ | Cl |
| X.45 | H | H | cyclohexyl | $CF_3$ | $CH_3$ | H |
| X.46 | H | H | cyclohexyl | $CF_2H$ | $CH_3$ | H |
| X.47 | H | H | cyclohexyl | $CFH_2$ | $CH_3$ | H |
| X.48 | H | H | cyclohexyl | $CF_2Cl$ | $CH_3$ | H |
| X.49 | F | F | cyclohexyl | $CF_3$ | $CH_3$ | H |
| X.50 | H | H | cyclohexyl | $CH_3$ | $CH_3$ | F |
| X.51 | H | H | cyclohexyl | $CH_3$ | $CH_3$ | Cl |
| X.52 | H | H | cycloheptyl | $CF_3$ | $CH_3$ | H |
| X.53 | H | H | cycloheptyl | $CF_3$ | $CH_2CH_3$ | H |
| X.54 | H | H | cycloheptyl | $CF_2H$ | $CH_3$ | H |
| X.55 | H | H | cycloheptyl | $CFH_2$ | $CH_3$ | H |
| X.56 | H | H | cycloheptyl | $CF_2Cl$ | $CH_3$ | F |
| X.57 | H | H | cycloheptyl | $CH_3$ | $CH_3$ | F |
| X.58 | H | H | cycloheptyl | $CH_3$ | $CH_3$ | Cl |
| X.59 | H | H | cyclooctyl | $CF_3$ | $CH_3$ | H |
| X.60 | H | H | cyclooctyl | $CF_2H$ | $CH_3$ | H |
| X.61 | H | H | phenyl | $CF_3$ | $CH_3$ | H |
| X.62 | H | H | phenyl | $CF_2H$ | $CH_3$ | H |
| X.63 | H | H | phenyl | $CFH_2$ | $CH_3$ | H |
| X.64 | H | H | phenyl | $CH_3$ | $CH_3$ | F |
| X.65 | H | H | phenyl | $CH_3$ | $CH_3$ | Cl |
| X.66 | H | H | 4-fluorophenyl | $CF_3$ | $CH_3$ | H |
| X.67 | H | H | 4-fluorophenyl | $CF_2H$ | $CH_3$ | H |
| X.68 | H | H | 4-chlorophenyl | $CF_3$ | $CH_3$ | H |
| X.69 | H | H | 4-chlorophenyl | $CF_2H$ | $CH_3$ | H |
| X.70 | H | H | 4-bromophenyl | $CF_3$ | $CH_3$ | H |
| X.71 | H | H | 4-bromophenyl | $CF_2H$ | $CH_3$ | H |
| X.72 | H | H | 2-thienyl | $CF_3$ | $CH_3$ | H |
| X.73 | H | H | 3-thienyl | $CF_3$ | $CH_3$ | H |
| X.74 | H | H | 2-furyl | $CF_3$ | $CH_3$ | H |
| X.75 | H | H | 2-furyl | $CF_3$ | $CH_3$ | H |
| X.76 | H | H | α-methylcyclopropyl | $CF_3$ | $CH_3$ | H |
| X.77 | H | H | α-methylcyclopropyl | $CF_2H$ | $CH_3$ | H |
| X.78 | H | H | α-methylcyclopropyl | $CH_3$ | $CH_3$ | F |
| X.79 | H | H | α-methylcyclopropyl | $CH_3$ | $CH_3$ | Cl |
| X.80 | H | H | α-methylcyclopropyl | $CF_3$ | $CH_3$ | Cl |

Table 2 provides 80 compounds of formula (1a):

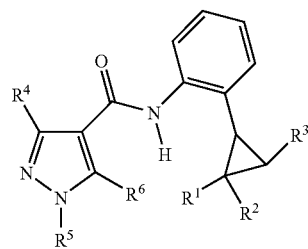

(Ia)

wherein $R^1$, $R^2$, $R^3$, $R^4$, $R^5$ and $R^6$ are as defined in Table 2.

Table 3 provides 80 compounds of formula (1b):

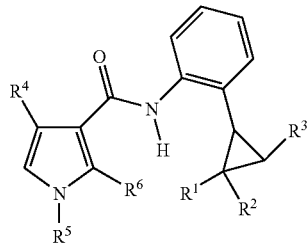

(Ib)

wherein $R^1$, $R^2$, $R^3$, $R^4$, $R^5$ and $R^6$ are as defined in Table 3.

Table 4 provides 50 compounds of formula (1c):

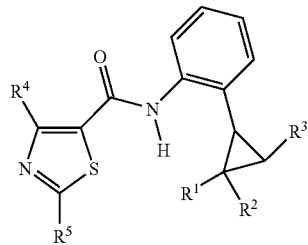

(Ic)

wherein $R^1$, $R^2$, $R^3$, $R^4$ and $R^5$ are as defined in Table 4.

TABLE 4

| Compound Number | $R^1$ | $R^2$ | $R^3$ | $R^4$ | $R^5$ |
|---|---|---|---|---|---|
| 4.1 | H | H | CH$_2$CH$_3$ | CF$_3$ | CH$_3$ |
| 4.2 | H | H | CH$_2$CH$_3$ | CH$_3$ | CH$_3$ |
| 4.3 | H | H | CH$_2$CH$_2$CH$_3$ | CF$_3$ | CH$_3$ |
| 4.4 | H | H | CH$_2$CH$_2$CH$_3$ | CH$_3$ | CH$_3$ |
| 4.5 | H | H | CH(CH$_3$)$_2$ | CF$_3$ | CH$_3$ |
| 4.6 | H | H | CH(CH$_3$)$_2$ | CH$_3$ | CH$_3$ |
| 4.7 | H | H | CH(CH$_3$)$_2$ | CH$_2$CH$_3$ | CH$_3$ |
| 4.8 | H | H | CH$_2$CH$_2$CH$_2$CH$_3$ | CF$_3$ | CH$_3$ |
| 4.9 | H | H | CH$_2$CH$_2$CH$_2$CH$_3$ | CH$_3$ | CH$_3$ |
| 4.10 | H | H | CH$_2$CH(CH$_3$)$_2$ | CF$_3$ | CH$_3$ |
| 4.11 | H | H | CH$_2$CH(CH$_3$)$_2$ | CH$_3$ | CH$_3$ |
| 4.12 | H | H | C(CH$_3$)$_3$ | CF$_3$ | CH$_3$ |
| 4.13 | H | H | CH$_2$CH$_2$CH$_2$CH$_2$CH$_3$ | CF$_3$ | CH$_3$ |
| 4.14 | H | H | CH$_2$CH$_2$CH$_2$CH$_2$CH$_3$ | CH$_3$ | CH$_3$ |
| 4.15 | H | H | CH$_2$CH$_2$CH(CH$_3$)$_2$ | CF$_3$ | CH$_3$ |
| 4.16 | H | H | CH$_2$CH$_2$CH(CH$_3$)$_2$ | CH$_3$ | CH$_3$ |
| 4.17 | H | H | CH$_2$CH$_2$CH(CH$_3$)$_2$ | CH$_3$ | CH$_2$CH$_3$ |
| 4.18 | H | H | CH$_2$CH$_2$CH$_2$CH$_2$CH$_2$CH$_3$ | CF$_3$ | CH$_3$ |
| 4.19 | H | H | CH$_2$CH$_2$CH$_2$CH$_2$CH$_2$CH$_3$ | CH$_3$ | CH$_3$ |
| 4.20 | H | H | cyclopropyl | CF$_3$ | CH$_3$ |
| 4.21 | H | H | cyclopropyl | CH$_3$ | CH$_3$ |
| 4.22 | H | H | cyclobutyl | CF$_3$ | CH$_3$ |
| 4.23 | H | H | cyclobutyl | CH$_3$ | CH$_3$ |
| 4.24 | H | H | cyclopentyl | CF$_3$ | CH$_3$ |
| 4.25 | H | H | cyclopentyl | CH$_3$ | CH$_3$ |
| 4.26 | H | H | cyclohexyl | CF$_3$ | CH$_3$ |
| 4.27 | H | H | cyclohexyl | CH$_3$ | CH$_3$ |
| 4.28 | H | H | cyclohexyl | CF$_3$ | CH$_2$CH$_3$ |
| 4.29 | H | H | cycloheptyl | CF$_3$ | CH$_3$ |
| 4.30 | H | H | cycloheptyl | CH$_3$ | CH$_3$ |
| 4.31 | H | H | cyclooctyl | CF$_3$ | CH$_3$ |
| 4.32 | H | H | cyclooctyl | CH$_3$ | CH$_3$ |
| 4.33 | H | H | phenyl | CF$_3$ | CH$_3$ |
| 4.34 | H | H | phenyl | CH$_3$ | CH$_3$ |
| 4.35 | H | H | 4-fluorophenyl | CF$_3$ | CH$_3$ |
| 4.36 | H | H | 4-fluorophenyl | CH$_3$ | CH$_3$ |
| 4.37 | H | H | 4-chlorophenyl | CF$_3$ | CH$_3$ |
| 4.38 | H | H | 4-chlorophenyl | CH$_3$ | CH$_3$ |
| 4.39 | H | H | 4-bromophenyl | CF$_3$ | CH$_3$ |
| 4.40 | H | H | 4-bromophenyl | CH$_3$ | CH$_3$ |
| 4.41 | H | H | 2-thienyl | CF$_3$ | CH$_3$ |
| 4.42 | H | H | 2-thienyl | CH$_3$ | CH$_3$ |
| 4.43 | H | H | 3-thienyl | CF$_3$ | CH$_3$ |
| 4.44 | H | H | 3-thienyl | CH$_3$ | CH$_3$ |
| 4.45 | H | H | 2-furyl | CF$_3$ | CH$_3$ |
| 4.46 | H | H | 2-furyl | CH$_3$ | CH$_3$ |
| 4.47 | H | H | 3-furyl | CF$_3$ | CH$_3$ |
| 4.48 | H | H | 3-furyl | CH$_3$ | CH$_3$ |
| 4.49 | H | H | α-methylcyclopropyl | CF$_3$ | CH$_3$ |
| 4.50 | H | H | α-methylcyclopropyl | CH$_3$ | CH$_3$ |

Table 5 provides 54 compounds of formula (1d):

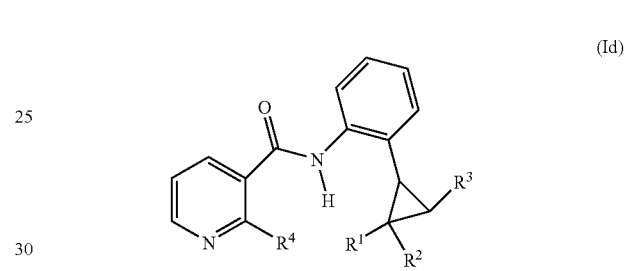

(Id)

wherein $R^1$, $R^2$, $R^3$ and $R^4$ are as defined in Table 5.

TABLE 5

| Compound Number | $R^1$ | $R^2$ | $R^3$ | $R^4$ |
|---|---|---|---|---|
| 5.1 | H | H | CH$_2$CH$_3$ | Cl |
| 5.2 | H | H | CH$_2$CH$_2$CH$_3$ | Cl |
| 5.3 | H | H | CH$_2$CH$_2$CH$_3$ | Br |
| 5.4 | H | H | CH$_2$CH$_2$CH$_3$ | CF$_3$ |
| 5.5 | H | H | CH(CH$_3$)$_2$ | Cl |
| 5.6 | H | H | CH(CH$_3$)$_2$ | Br |
| 5.7 | H | H | CH(CH$_3$)$_2$ | CF$_3$ |
| 5.8 | H | H | CH$_2$CH$_2$CH$_2$CH$_3$ | Cl |
| 5.9 | H | H | CH$_2$CH$_2$CH$_2$CH$_3$ | Br |
| 5.10 | H | H | CH$_2$CH$_2$CH$_2$CH$_3$ | CF$_3$ |
| 5.11 | H | H | C(CH$_3$)$_3$ | Cl |
| 5.12 | H | H | CH$_2$CH(CH$_3$)$_2$ | Cl |
| 5.13 | H | H | CH$_2$CH(CH$_3$)$_2$ | Br |
| 5.14 | H | H | CH$_2$CH(CH$_3$)$_2$ | CF$_3$ |
| 5.15 | H | H | CH$_2$CH$_2$CH$_2$CH$_2$CH$_3$ | Cl |
| 5.16 | H | H | CH$_2$CH$_2$CH$_2$CH$_2$CH$_3$ | Br |
| 5.17 | H | H | CH$_2$CH$_2$CH(CH$_3$)$_2$ | Cl |
| 5.18 | H | H | CH$_2$CH$_2$CH(CH$_3$)$_2$ | Br |
| 5.19 | H | H | CH$_2$CH$_2$CH$_2$CH$_2$CH$_2$CH$_3$ | Cl |
| 5.20 | H | H | CH$_2$CH$_2$CH$_2$CH$_2$CH$_2$CH$_3$ | Br |
| 5.21 | H | H | cyclopropyl | Cl |
| 5.22 | H | H | cyclopropyl | Br |
| 5.23 | H | H | cyclobutyl | Cl |
| 5.24 | H | H | cyclobutyl | Br |
| 5.25 | H | H | cyclopentyl | Cl |
| 5.26 | H | H | cyclopentyl | Br |
| 5.27 | F | F | cyclopentyl | CF$_3$ |
| 5.28 | H | H | cyclohexyl | Cl |
| 5.29 | H | H | cyclohexyl | Br |
| 5.30 | H | H | cyclohexyl | CF$_3$ |
| 5.31 | H | H | cycloheptyl | Cl |
| 5.32 | H | H | cycloheptyl | Br |
| 5.33 | H | H | cycloheptyl | CF$_3$ |
| 5.34 | H | H | cyclooctyl | Cl |
| 5.35 | H | H | phenyl | Cl |

TABLE 5-continued

| Compound Number | R$^1$ | R$^2$ | R$^3$ | R$^4$ |
|---|---|---|---|---|
| 5.36 | H | H | phenyl | Br |
| 5.37 | H | H | 4-fluorophenyl | Cl |
| 5.38 | H | H | 4-fluorophenyl | Br |
| 5.39 | H | H | 4-fluorophenyl | CF$_3$ |
| 5.40 | H | H | 4-chlorophenyl | Cl |
| 5.41 | H | H | 4-chlorophenyl | Br |
| 5.42 | H | H | 4-chlorophenyl | CF$_3$ |
| 5.43 | H | H | 4-bromophenyl | Cl |
| 5.44 | H | H | 2-thienyl | Cl |
| 5.45 | H | H | 2-thienyl | Br |
| 5.46 | H | H | 3-thienyl | Cl |
| 5.47 | H | H | 3-thienyl | Cl |
| 5.48 | H | H | 2-furyl | Cl |
| 5.49 | H | H | 2-furyl | Br |
| 5.50 | H | H | 3-furyl | Cl |
| 5.51 | H | H | 3-furyl | Br |
| 5.52 | H | H | 2-pyridyl | Cl |
| 5.53 | H | H | α-methylcyclopropyl | Cl |
| 5.54 | H | H | α-methylcyclopropyl | Br |

Table 6 provides 45 compounds of formula (1e):

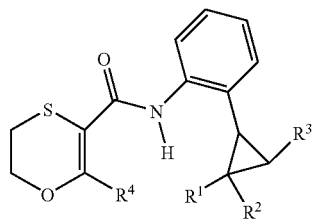

(Ie)

wherein R$^1$, R$^2$, R$^3$ and R$^4$ are as defined in Table 6.

TABLE 6

| Compound Number | R$^1$ | R$^2$ | R$^3$ | R$^4$ |
|---|---|---|---|---|
| 6.1 | H | H | CH$_2$CH$_3$ | CH$_3$ |
| 6.2 | H | H | CH$_2$CH$_2$CH$_3$ | CF$_3$ |
| 6.3 | H | H | CH$_2$CH$_2$CH$_3$ | CH$_3$ |
| 6.4 | H | H | CH(CH$_3$)$_2$ | CF$_3$ |
| 6.5 | H | H | CH(CH$_3$)$_2$ | CH$_3$ |
| 6.6 | H | H | CH$_2$CH$_2$CH$_2$CH$_3$ | CF$_3$ |
| 6.7 | H | H | CH$_2$CH$_2$CH$_2$CH$_3$ | CH$_3$ |
| 6.8 | H | H | CH$_2$CH(CH$_3$)$_2$ | CF$_3$ |
| 6.9 | H | H | CH$_2$CH(CH$_3$)$_2$ | CH$_3$ |
| 6.10 | H | H | C(CH$_3$)$_3$ | CF$_3$ |
| 6.11 | H | H | C(CH$_3$)$_3$ | CH$_3$ |
| 6.12 | H | H | CH$_2$CH$_2$CH$_2$CH$_2$CH$_3$ | CF$_3$ |
| 6.13 | H | H | CH$_2$CH$_2$CH$_2$CH$_2$CH$_3$ | CH$_3$ |
| 6.14 | H | H | CH$_2$CH$_2$CH(CH$_3$)$_2$ | CF$_3$ |
| 6.15 | H | H | CH$_2$CH$_2$CH(CH$_3$)$_2$ | CH$_3$ |
| 6.16 | H | H | CH$_2$CH$_2$CH$_2$CH$_2$CH$_2$CH$_3$ | CF$_3$ |

TABLE 6-continued

| Compound Number | R$^1$ | R$^2$ | R$^3$ | R$^4$ |
|---|---|---|---|---|
| 6.17 | H | H | CH$_2$CH$_2$CH$_2$CH$_2$CH$_2$CH$_3$ | CH$_3$ |
| 6.18 | H | H | cyclopropyl | CF$_3$ |
| 6.19 | H | H | cyclopropyl | CH$_3$ |
| 6.20 | H | H | cyclobutyl | CF$_3$ |
| 6.21 | H | H | cyclobutyl | CH$_3$ |
| 6.22 | H | H | cyclohexyl | CF$_3$ |
| 6.23 | H | H | cyclohexyl | CH$_3$ |
| 6.24 | H | H | cycloheptyl | CF$_3$ |
| 6.25 | F | F | cycloheptyl | CH$_3$ |
| 6.26 | H | H | cyclooctyl | CF$_3$ |
| 6.27 | H | H | cyclooctyl | CH$_3$ |
| 6.28 | F | F | cyclooctyl | CF$_3$ |
| 6.29 | H | H | phenyl | CF$_3$ |
| 6.30 | H | H | phenyl | CH$_3$ |
| 6.31 | H | H | 4-fluorophenyl | CF$_3$ |
| 6.32 | H | H | 4-flurophenyl | CH$_3$ |
| 6.33 | H | H | 4-chlorophenyl | CF$_3$ |
| 6.34 | H | H | 4-chlorophenyl | CH$_3$ |
| 6.35 | H | H | 4-bromophenyl | CF$_3$ |
| 6.36 | H | H | 2-thienyl | CF$_3$ |
| 6.37 | H | H | 2-thienyl | CH$_3$ |
| 6.38 | H | H | 3-thienyl | CF$_3$ |
| 6.39 | H | H | 3-thienyl | CH$_3$ |
| 6.40 | H | H | 2-furyl | CF$_3$ |
| 6.41 | H | H | 3-furyl | CF$_3$ |
| 6.42 | H | H | 2-pyridyl | CF$_3$ |
| 6.43 | H | H | 4-pyridyl | CF$_3$ |
| 6.44 | H | H | α-methylcyclopropyl | CF$_3$ |
| 6.45 | H | H | α-methylcyclopropyl | CH$_3$ |

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

Table 7 shows selected melting point and selected NMR data, all with CDCl$_3$ as the solvent (unless otherwise stated; if a mixture of solvents is present, this is indicated as, for example, (CDCl$_3$/d$_6$-DMSO)), (no attempt is made to list all characterising data in all cases) for compounds of Tables 1 to 6. Unless otherwise stated, the data relate to a cis/trans mixture of each compound; a compound number which ends with the letter 'c' relates only to its cis-isomer and a compound number which ends with the letter 't' relates only to its trans-isomer.

TABLE 7

| Compound Number | $^1$H-NMR data: (ppm/multiplicity/number of Hs). | m.p./ (° C.) |
|---|---|---|
| 1.3 | 0.6-0.90/m/8H(cis and trans); 1.02/d/6H(cis); 1.11/6H(trans); 1.48/m/1H(trans); 1.78/m/1H(cis); 3.83/s/4H(NH$_2$ cis and trans); 6.68/m/4H(cis and trans); 7.0/m/4H(cis and trans). | oil |
| 1.5 | 0.6-1.1/m/6H(cis and trans); 0.95-101/2d/12H(cis and trans); 1.25/m/2H(cis or trans); 1.40/m/2H(cis or trans); 1.78/m/2H(cis or trans); 3.85/s/4H(NH$_2$ cis and trans); 6.70/m/4H(cis and trans); 7.0/m/4H(cis and trans). | oil |

TABLE 7-continued

| Compound Number | ¹H-NMR data: (ppm/multiplicity/number of Hs). | m.p./ (° C.) |
|---|---|---|
| 1.6t | 0.52/m/1H; 0.80/m/1H; 0.97/s/9H; 1.08/m/1H; 1.57/m/1H; 3.85/s/2H; 6.68/m/2H; 7.0/m/2H. | oil |
| 1.10c | 0.01/m/2H, 0.11/m/1H; 0.22/m/1H; 0.58/m/1H; 0.69/m/1H; 0.85/m/1H; 1.67/m/1H; 3.75/s/2H(NH$_2$); 6.49-6.60/m/2H; 6.82-7.00/m/2H. | oil |
| 1.10t | 0.01/m/2H; 0.30/m/2H; 0.55/m/2H; 0.72/m/2H; 1.28/m/1H; 3.70/s/2H(NH$_2$); 6.45-6.55/m/2H; 6.77-6.85/m/2H. | oil |
| 1.12 | 0.75/m/4H (cis and trans); 0.97/m/2H (cis and trans); 1.3-1.95/m/20H (cis and trans); 3.88/s/4H (cis and trans); 6.68/m/4H (cis and trans); 7.01/m/4H (cis and trans). | oil |
| 1.13 | 0.62-1.98/m/30H(cis and trans); 3.80/s/4H(cis and trans); 6.65/m/4H(cis and trans); 6.97/m/4H(cis and trans). | oil |
| 1.17c | | 110-112 |
| 1.17t | | 69-70 |
| 1.18c | 1.29/m/1H; 1.52/m/1H; 2.20/m/1H; 2.42/m/1H; 3.55/s/2H; 6.50/d/1H; 6.65-6.85/m/5H; 6.99/t/1H; 7.09/d/1H. | oil |
| 1.18t | | 95-97 |
| 1.22c | | 60-62 |
| 1.22t | 0.01-0.1/m/4H; 0.42/m/2H; 0.99/s/3H; 1.01/m/1H; 1.21/m/1H; 3.55/s/2H; 6.45/m/2H; 6.78/m/2H. | oil |
| 2.5 | | 99-102 |
| 2.17 | | 75-78 |
| 2.18 | | 74-79 |
| 2.23 | | 134-136 |
| 2.24 | | 110-112 |
| 2.33 | | 88-92 |
| 2.34c | | 111-113 |
| 2.34t | | 116-118 |
| 2.35c | | 93-95 |
| 2.35t | | 134-136 |
| 2.45 | 0.6-1.90/m/30H(cis and trans); 4.0/s/6H(cis and trans); 7.0-7.28/m/6H(cis and trans); 8.0/s/1H(trans); 8.05/s/1H(cis); 8.12/d/2H(trans); 8.20/d/2H(cis). | resin |
| 2.46t | | 116-118 |
| 2.52 | | 116-118 |
| 2.54 | | 129-131 |
| 2.57 | | 107-109 |
| 2.66c | | resin |
| 2.66t | | 145-147 |
| 2.67c | | 104-106 |
| 2.67t | | 160-161 |
| 2.68c | | resin |
| 2.68t | | 148-150 |
| 2.69c | | 145-147 |
| 2.69t | | 149-150 |
| 2.76c | | 119-121 |
| 2.76t | | 107-108 |
| 2.77c | | 82-84 |
| 2.77t | | 109-111 |
| 2.78c | | 119-122 |
| 2.78t | | 96-97 |
| 3.5 | | 74-78 |
| 3.17 | | 61-65 |
| 3.23 | | 92-96 |
| 3.33 | −0.1-0.90/m/16H (cis and trans); 1.45/m/1H(trans); 1.79/m/1H(cis); 3.58/s/6H (cis and trans); 6.82-7.13/m/10H(cis and trans); 7.92/s/1 (NH-trans); 8.03/dd/1H(trans); 8.10/s/1H(NH-cis); 8.19/dd/1H (cis). | resin |
| 3.39 | 0.63-1.83/m/26H(cis and trans); 3.72/s/6H(cis and trans); 6.95-7.38/m/10H(cis and trans); 8.05/s/1H(NH-trans); 8.18/dd/1H(trans); 8.30/dd/1H(cis). | resin |
| 3.45 | 0.6-1.90/m/30H(cis and trans); 3.70/s/6H(cis and trans); 6.98-7.35/m/8H(cis and trans); 8.08/s(broad)/2H(cis and trans); 8.17/d/2H(trans); 8.25/d/2H(cis). | resin |
| 3.66c | 1.40/m/1H; 1.50-1.65/m/1H; 2.37/m/1H, 2.50/m/1H; 3.73/s/3H; 6.60-6.70/m/5H; 6.97/m/2H; 7.18/m/3H; 7.82/s/1H(NH); 8.02/d/1H. | resin |
| 3.66t | | 146-148 |
| 3.68c | 1.40/m/1H; 1.57/m/1H; 2.40/m/2H; 3.72/s/3H; 6.68/d/2H; 6.90-7.08/m/4H; 7.18/m/3H; 7.80/s/1H; 8.02/d/1H. | resin |
| 3.68t | | 150-152 |
| 3.76 | | resin |
| 3.80c | | 123-126 |
| 3.80t | | 94-96 |
| 4.10 | | 69-74 |
| 4.12 | | resin |
| 4.24 | | 113-115 |

TABLE 7-continued

| Compound Number | $^1$H-NMR data: (ppm/multiplicity/number of Hs). | m.p./ (° C.) |
|---|---|---|
| 4.26 | | 138-142 |
| 5.5 | | resin |
| 5.12 | | 83-86 |
| 5.21c | | 75-77 |
| 5.21t | | 80-82 |
| 5.25 | | 131-133 |
| 5.28 | | 115-119 |
| 5.37c | | 164-166 |
| 5.37t | | 133-135 |
| 5.40c | | 160-162 |
| 5.40t | | 136-138 |
| 5.53c | −0.25/m/1H; −0.01-0.03/m/3H; 0.60/s/3H; 0.65/m/1H; 0.79/m/1H; 1.25/m/1H; 1.80/m/1H; 6.95/t/1H; 7.08/m/2H; 7.28/m/1H; 8.15/d/2H; 8.38/m/1H; 8.62/s/1H(NH). | resin |
| 5.53t | 0.01/m/4H; 0.58/m/2H; 0.94/s/3H; 1.11/m/1H; 1.44/m/1H; 6.98/m/2H; 7.09/m/1H; 7.23/m/1H; 8.01/dd/1H; 8.10/d/1H; 8.35/dd/1H; 8.40/s/1H. | resin |
| 6.10 | | resin |

The compounds according to formula (I) may be prepared according to the following reaction schemes.

Scheme 1A

A compound of formula (II) [where R$^3$ is as defined above for a compound of formula (I)] may be prepared by a reaction sequence starting with a crossed-aldol condensation of benzaldehyde with a ketone of formula CH$_3$C(O)R$^3$ [where R$^3$ is as defined above for a compound of formula (I)] in the presence of NaOH or KOH in a solvent (such as water or ethanol) and usually under reflux conditions or alternatively by reaction of benzaldehyde with a Wittig reagent under standard conditions. The resulting α,β-unsaturated ketone of formula (III) [where R$^3$ is as defined above for a compound of formula (I)]:

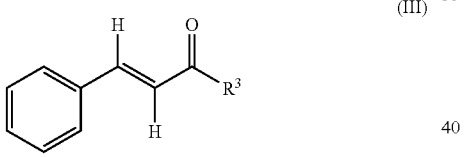

(III)

may then be converted into a compound of formula (IV) [where R$^3$ is as defined above for a compound of formula (I)]:

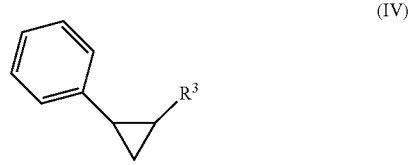

(IV)

by reacting first with hydrazine hydrate in ethanol under reflux conditions and then heating (in the range 150 to 250° C.) in the presence of KOH (distilling off the solvent). After nitration with HNO$_3$/H$_2$O or HNO$_3$/acetic anhydride in a cooled vessel (in the range −30° C. to 0° C.), the resultant o/p-mixture of nitrobenzene of formula (V) [where R$^3$ is as defined above for a compound of formula (I)]:

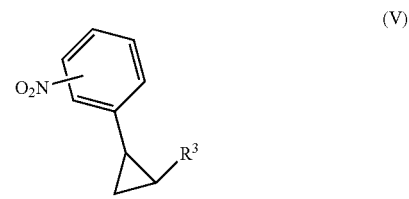

(V)

may then be separated and catalytically reduced (Pt/C/H$_2$ or Ra—Ni/H$_2$) in a solvent (such as methanol, ethanol or THF) at room temperature, to produce a crude o/p-mixture of a compound of formula (II), which may be further purified by standard techniques.

Alternatively, a compound of formula (II) [where R$^3$ is as defined above for a compound of formula (1)] may be prepared by a process as illustrated by the following reaction sequence and which involves a Pd(II)-catalysed imination step.

Scheme 1B

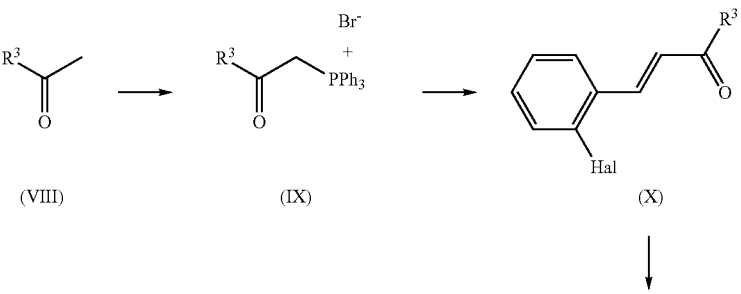

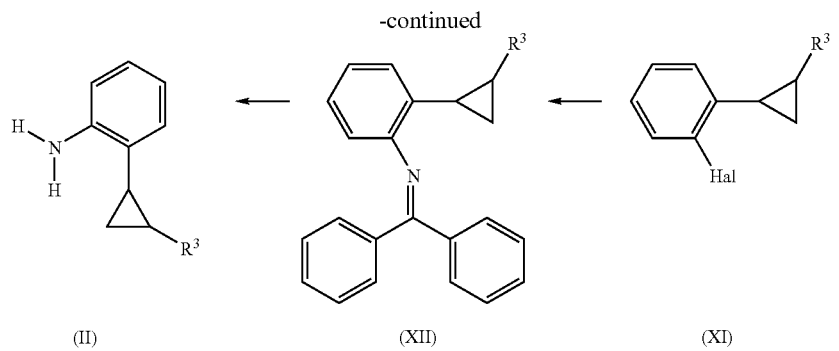

(II)    (XII)    (XI)

A compound of formula (VII) [where $R^3$ is as defined above for a compound of formula (I)] is added to bromine and methanol at a temperature of 5-10° C., after which triphenylphosphine in a solvent (such as tetrahydrofuran) is added, to produce a compound of formula (IX) [where $R^3$ is as defined above for a compound of formula (I)], which in turn is added to sodium hydride, in a solvent [such as DMSO], and then reacted with 2-bromobenzaldehyde or 2-iodobenzaldehyde to yield a compound of formula (X) [where $R^3$ is as defined above for a compound of formula (I) and Hal is bromo or iodo]. The resultant compound of formula (X) is then mixed with hydrazine hydrate in a solvent [such as ethanol] and heated to reflux, after which potassium hydroxide is added and the resultant reaction mixture is maintained at 200-220° C. for several hours. A standard extraction and purification procedure yields a compound of formula (XI) [where $R^3$ is as defined above for a compound of formula (I) and Hal is bromo or iodo] which may then be converted to a compound of formula (II) by mixing with benzophenone imine, sodium tertiary butoxide, tris-dibenzylideneacetone-dipalladium (Pd$_2$dba$_3$), racemic 2,2'-bis(diphenylphosphino)-1,1' binaphthyl (BINAP) and a solvent [such as benzene or toluene] and heating at reflux temperature, typically for several hours, and adding the resultant [usually crude isolated] imine to a mixture of hydroxylamine hydrochloride, sodium acetate and a solvent [such as methanol]. The resultant mixture is stirred, preferably for about an hour at room temperature, after which a cis-/trans-mixture of a compound of formula (1H) may be extracted and subsequent separation of the cis- and trans-isomers achieved by using flash chromatography.

In the above illustrated Pd-catalysed imination process, instead of the catalyst-ligand-system Pd$_2$dba$_3$/BINAP, the system palladium diacetate/1,1'-bis(diphenyl-phosphino)ferrocene (dppf) could be used as an alternative.

Reaction scheme 1B is novel and inventive, particularly the use of a Pd(II)-catalysed imination step. Therefore in a still further aspect the present invention provides a process for preparing a compound of formula (II), where $R^3$ is as defined above, comprising at least one of the steps of reaction scheme 1B; in particular a step using a Pd(II)catalyst-ligand-system [where the ligand is selected from a suitable sterically demanding phosphine (for example BINAP or dppf)] to react a compound of formula (XI) [where Hal is bromo or iodo; and $R^3$ is as defined above] with benzophenone imine optionally in the presence of a base [such as sodium-tert-butanolate, potassium-tert-butananolate, sodium carbonate, potassium carbonate or cesium carbonate] to produce a compound of formula (XII) [where $R^3$ is as defined above].

Examples of imination reactions with benzophenone imine are provided in the literature (Journal of Organometallic Chemistry, 1999, 576, 125-146 and Tetrahedron Letters 1997, 38, 6367-6370).

Scheme 2

The synthesis of an amine of formula (IIA)

(IIA)

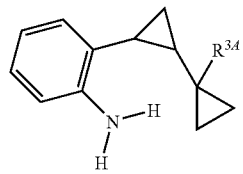

[where $R^{3A}$ is hydrogen or methyl] may be accomplished by a reaction sequence started by a Wittig reaction of o-nitrobenzaldehyde with an ylide [prepared from a cyclopropylmethlytriphenylphosphonium bromide in the presence of a strong base, such as NaH in a solvent such as DMSO, in the range 0-85° C.]. The resulting E/Z-mixture of a compound of formula (VI)

(VI)

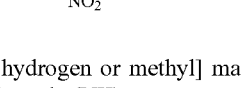

[where $R^{3A}$ is hydrogen or methyl] may be converted to a compound of formula (VII)

(VII)

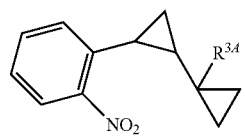

by the application of the Simmons Smith reaction (Zn/Cu, CH$_2$I$_2$, ether as solvent) to the olefin group of the compound of formula (VI). The reduction of the nitro group of the corresponding compound of formula (VII) may be performed using the conditions described in Scheme 1, to produce a compound of formula (IIA).

Scheme 3

A compound of formula (1) may be prepared by reacting a compound of formula It Het-C(=O)—R* [where R* is halogen, hydroxy or C$_{1-6}$ alkoxy, but preferably chloro] with a compound of formula (II) as prepared above in the presence of a base (such as triethylamine, Hunig base, sodium bicarbonate, sodium carbonate, potassium carbonate, pyridine or quinoline, but preferably triethylamine) and in a solvent (such as diethylether, TBME, THF, dichloromethane, chloroform, DMF or NMP) for between 10 minutes and 48 hours (preferably 12 to 24 hours) and between 0° C. and reflux (preferably 20 to 25° C.). When R* is hydroxy, a coupling agent [such as benzotriazol-1-yloxytris(dimethylamino) phosphoniumbexafluorophosphate, bis-(2-oxo-3-oxazolidinyl)-phosphinic acid chloride, N,N'-dicyclohexylcarbodiimide or 1,1'-carbonyl-diimidazole] may be used.

Scheme 4

A compound of formula (IA)

(IA)

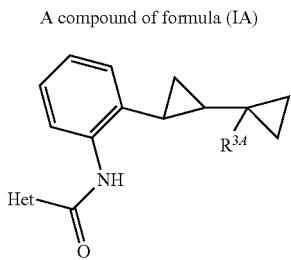

[where $R^{3A}$ is hydrogen or methyl] may be prepared by the reduction of the nitro group of a compound of formula (VI) [where $R^{3A}$ is hydrogen or methyl] using standard conditions (for example, catalytic reduction or Béchamp-reduction) followed by amidation with an acid chloride to provide a compound of formula (VII) [where $R^{3A}$ is hydrogen or methyl]

(VII)

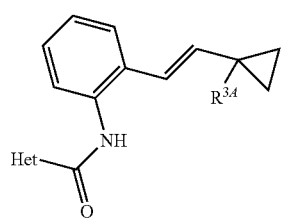

which is subsequently used in a Simmons-Smith reaction (Zn/Cu,CH$_2$I$_2$, ether as solvent) to provide a compound of formula (IA).

Surprisingly, it has now been found that the novel compounds of formula (1) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (1) are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) can be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancyrmidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymnidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimlides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, toiclofos-methyl; various others, such as acibenzolar-S-methyl, anilazine, benthiavalicarb, blasticidin-S, chinomethionate, chloroneb, chlorothalonil, cyflufenarnid, cymoxanil, dichione, diclomezine, dicloran, diethofencarb, dimethomorph, SYP-LI90 (proposed name: flumorph), dithianon, ethaboxam, etridiazole, famoxadone, fenamidone, fenoxanil, to fentin, ferimzone, fluazinam, flusulfamide, fenhexamid, fosetyl-alurminium, hymexazol, iprovalicarb, IF-916 (cyazofanrid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (D), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula 1, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound No. 1.5.

To a mixture of 17.4 g (0.1 mol) (2-isobutyl-cyclopropyl) benzene and 80 ml of acetic acid anhydride was added a solution of 6.0 g (0.095 mol) nitric acid and 40 ml acetic acid anhydride in such a manner that the internal temperature was kept constant at −30° C. The resulting reaction mixture was stirred for 1 hour at −30° C. and then for 2 hours at 0° C. Then the mixture was poured onto 500 ml of ice water and extracted three times with hexane. The hexane phases were combined and twice washed with 5% aqueous bicarbonate solution. After drying of the organic phase over sodium sulphate and distilling off the solvent in a water jet vacuum, the crude reaction product was obtained. Purification by flash chromatography over silica get (eluant: ethylacetate/hexane 1:10) yielded 10.5 g of a yellow oil (mixture of para- and ortho-nitroisomers) which was directly used in the next step. This isomeric mixture [consisting of 10.5 g (0.048 mol) 1-(2-isobutyl-cycloproply)2-nitrobenzene and 1-(2-isobutyl-cyclopropyl)$_4$-nitrobenzene] was dissolved in 110 ml of ethanol and hydrogenated over 5% Pt/C catalyst for 45 minutes. After the theoretical uptake of hydrogen had occurred, the catalyst was filtered off and the solvent was removed in vacuo. The crude isomeric aniline mixture was purified by flash chromatography (eluant: ethylacetate/hexane 1:2).

Yield: 6.38 g of 2-(2-isobutyl-cyclopropyl)phenyl amine was obtained as a yellow oil (cis/trans mixture).

EXAMPLE 2

This Example illustrates the preparation of Compound 3.17.

A solution of 0.35 g (0.0018 mol) 1-methyl-4-trifluoromethyl-pyrrole-3-carboxylic acid and 0.24 g (0.0019 mol) oxalylchloride in 15 ml methylenechloride was stirred for 3 hours at room temperature in the presence of two drops of absolute DMF. Then the acid chloride solution was slowly added to a solution of 0.34 g (0.0018 mol) 2-(2-isobutyl-cyclopropyl) phenylamine, 0.27 g (0.0027 mol) triethylamine and 10 ml methylene chloride. The resulting mixture was then stirred for 16 hours at room temperature. After removal of the solvent in vacuo, the crude material was taken up in ca. 100 ml ethylacetate. The ethylacetate phase was twice washed with water and after drying the organic phase, the solvent was again distilled off in a water jet vacuum. The crude product was purified by flash chromatography (eluant: hexane/ethylacetate/methylene chloride 1:2:2).

Yield: 0.52 g 1-methyl-4-trifluoromethyl-1H-pyrrole-3-carboxylic acid [2-(2-isobutyl-cyclopropyl)phenyl]amide in the form of a white powder (cis/trans-mixture).

EXAMPLE 3

This Example illustrates the preparation of Compound Nos. 1.10c and 1.10t.
Step 1:
In a sulfonation flask, NaH (12.8 g; 0.32 mol) was added to absolute DMSO (600 ml). After heating at 80° C. for 90 minutes, cyclopropylcarbonylmethyltriphenyl phosphoniumbromide (136.5 g; 0.32 mol) was added portionwise at room temperature. The resultant suspension was stirred for 30 minutes at room temperature and then a solution of 2-bromobenzaldehyde (59.4 g; 0.32 mol) in absolute DMSO (100 ml) was added dropwise. After heating the resultant mixture for 4 hours at 50° C., the mixture was poured onto 2.5 litres of ice water. Extraction with ethylacetate, drying over sodium sulfate and distilling off the solvent in a water jet vacuum yielded the crude product. Purification was achieved by vacuum distillation.

Yield: 77.6 g of E-3-(2-bromophenyl)-1-cyclo-propylpropenone as a yellow oil (b.p.: 125-130° C. at 0.3 mbar).
Step 2:
In a sulfonation flask, a mixture of E-3-(2-bromophenyl)-1-cyclo-propylpropenone (776 g; 0.309 mol) and hydrazine hydrate (23.2 g; 0.464 mol) in ethanol (25 ml) was heated at reflux temperature for 2 hours. Then powdered potassium hydroxide (85%) (24.4 g; 0.37 mol) was added and the excesses of hydrazine hydrate and solvent were distilled out of the flask. The remaining mixture was then heated at a temperature of 205-210° C. for 3 hours. The resultant resin was dissolved in ethylacetate (500 ml) at a temperature of 50° C. and the organic phase was washed twice with water. Drying of the ethylacetate phase over sodium sulfate and distilling off the solvent in a water jet vacuum gave the raw material, which was purified by flash chromatography over silica gel (eluant: hexane/methylene chloride 7:1).

Yield: 61.2 g of 2-(2-bromophenyl)bicyclopropyl in the form of a slightly yellowish oil (cis/trans-mixture).
Step 3:
A mixture of 2-(2-bromophenyl)bicyclopropyl (28.5 g; 0.12 mol), benzophenoneimine (26.1 g; 0.144 mol), sodium tertiary butoxide (16.1 g; 0.168 mol), tris-dibenzyl-idenea-cetonedipalladium ($Pd_2$ $dba_3$) (0.43 g; 0.474 mmol), racemic 2,2'-bis(diphenylphosphino)1,1'-binaphthyl (BINAP) (0.83 g; 1.34 mmol) and absolute toluene (450 ml) was heated at reflux temperature under an atmosphere of nitrogen for 6 hours. Then the solvent was removed in a water jet vacuum and the residue was taken up in ethylacetate (750 ml). The organic layer was washed three times with brine and then dried over sodium sulfate. After evaporation of the solvent, the crude product was obtained. Purification was achieved by using flash chromatography over silica gel (eluant: hexane/methylene chloride 5:1).

Yield: 39.9 g of cis-/trans-mixture of benzhydrilidene (2-bi-cyclopropyl-2-yl-phenyl)amine in the form of a brownish oil.
Step 4:
In a sulfonation flask, hydroxylamine hydrochloride (0.35 g; 0.0048 mol), sodium acetate (0.53 g; 0.0064 mol) and absolute methanol (30 ml) were stirred at room temperature for about 15 minutes. Then a solution of benzhydrilidene (2-bicyclopropyl-2-yl-phenyl)amine (0.9 g; 0.00267 mol) in methanol (15 ml) was added dropwise. The resultant mixture was stirred for 1 hour at room temperature. After dilution with ethylacetate (250 ml), the organic phase was washed twice with water. After drying the organic phase (sodium sulfate) and distilling off the solvent in a water jet vacuum, the crude product was obtained. The final purification and separation of the cis- and trans-isomers was achieved by using flash chromatography (eluant: hexane/ethylacetate 5:1).

Yield: 0.21 g of trans- and 0.15 g of cis-2-bicyclopropyl-2-yl-phenylamine in the form of brownish oils.

FORMULATION EXAMPLES FOR COMPOUNDS OF FORMULA (D)

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia recondita*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation.

Compounds of Tables 2, 3, 4 and 5 show good activity in this test (<20% infestation). Infestation is prevented virtually completely (0-5% infestation) with each of compounds 2.5, 2.17, 2.18, 2.23, 2.24, 2.33, 2.45, 2.46t, 2.76c, 2.76t, 2.77c, 2.77t, 3.5, 3.17, 3.23, 3.33, 3.45, 3.76, 4.10, 4.12, 4.26, 5.5, 5.12, 5.21c and 5.37c.

Example B-2

Action Against *Podosphaera leucotricha*/Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds of Tables 2, 3 and 4 show good activity in this test. The compounds 2.5, 2.17, 2.18, 2.23, 2.24, 2.33, 2.45, 2.46t, 3.5, 3.17, 3.23, 3.33, 3.45, 4.10 and 4.12 each exhibit strong efficacy (<20% infestation).

Example B-3

Action Against *Venturia Inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds of Tables 2 and 3 show good activity in this test. The compounds 2.5, 2.17, 2.18, 2.23, 2.24, 2.33, 2.45, 2.46t, 3.5, 3.17, 3.23, 3.33 and 3.45 each exhibit strong efficacy (<20% infestation).

Example B4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r.h. in a greenhouse the disease incidence is assessed.

Compounds of Tables 2, 3 and 4 show good activity in this test. The compounds 2.5, 2.17, 2.18, 2.23, 2.24, 2.45, 2.46t, 2.77c, 2.77t, 3.5, 3.17, 3.23, 3.45, 4.10 and 4.12 each exhibit strong efficacy (<20% infestation).

Example B-5

Action Against *Botrytis cinerea*/Apple (*Botrytis* on Apple Fruits)

In an apple fruit cv. Golden Delicious 3 holes are drilled and each filled with 30 µl droplets of the formulated test compound (0.002% active ingredient). Two hours after application 50 µl of a spore suspension of *B. cinerea* ($4 \times 10^5$ conidia/ml) are pipetted on the application sites. After an incubation period of 7 days at 22° C. in a growth chamber the disease incidence is assessed.

Compounds of Tables 2, 3, 4, 5 and 6 show good activity in this test. The compounds 2.5, 2.17, 2.18, 2.23, 2.24, 2.33, 2.45, 2.46t, 2.76c, 2.76t, 2.77c, 2.77t, 3.5, 3.17, 3.23, 3.33, 3.76, 3.45, 3.76, 4.10, 4.12, 4.26, 5.5, 5.12, 5.21c and 5.37 each exhibit very strong efficacy (<10% infestation).

Example B-6

Action Against *Botrytis cinerea*/Grape (*Botrytis* on Grapes)

5 week old grape seedlings cv. Gutedel are treated with the formulated test compound (0.002% active ingredient) in a spray chamber. Two days after application grape plants are inoculated by spraying a spore suspension $1 \times 10^6$ conidia/ml) on the test plants. After an incubation period of 4 days at 21° C. and 95% r.h. in a greenhouse the disease incidence is assessed.

Compounds of Tables 2, 3, 4, 5 and 6 show good activity in this test. The compounds 2.5, 2.17, 2.18, 2.23, 2.24, 2.45, 2.46t, 2.76c, 2.76t, 2.77c, 2.77t, 3.5, 3.17, 3.23, 3.33, 3.39, 3.76, 4.10, 4.12, 4.26, 5.5, 5.12, 5.21c and 5.37c each exhibit very strong efficacy (<10% infestation).

Example B-7

Action Against *Botrytis cinerea*/Tomato (*Botrytis* on Tomatoes)

4 week old tomato plants cv. Roter Gnom are treated with the formulated test compound (0.002% active ingredient) in a spray chamber. Two days after application tomato plants are inoculated by spraying a spore suspension $1 \times 10^5$ conidia/ml) on the test plants. After an incubation period of 4 days at 20° C. and 95% r.h. in a growth chamber the disease incidence is assessed.

Compounds of Tables 2, 3, 4, 5 and 6 show good activity in this test. The compounds 2.5, 2.17, 2.18, 2.23, 2.24, 2.33, 2.45, 2.46t, 2.76c, 2.76t, 2.77c, 2.77t, 3.5, 3.17, 3.23, 3.39, 3.45, 3.76, 4.10, 4.12, 4.26, 5.5, 5.12, 5.21c and 5.37c each exhibit very strong efficacy (<10% infestation).

Example B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3 \times 10^4$ conidia/ml) on the test plants. After an incubation period of 2 days at 20° C. and 95% r.h. plants are kept for 2 days at 20° C. and 60% r.h. in a greenhouse. The disease incidence is assessed 4 days after inoculation.

Compounds of Tables 2, 3, 4, 5 and 6 show good activity in this test. The compounds 2.5, 2.17, 2.18, 2.23, 2.24, 2.33, 2.45, 2.46t, 2.76c, 2.76t, 2.77c, 2.77t, 3.5, 3.17, 3.23, 3.39, 3.45, 3.76, 4.10, 4.12, 4.26, 5.5, 5.12, 5.21c and 5.37c each exhibit very strong efficacy (<20% infestation).

Example B-9

Action Against *Septoria nodorum*/Wheat (*Septoria* Leaf Spot on Wheat)

1 week old wheat plants cv. Arina are treated with the formulated test compound (0.02% active ingredient) in a spray chamber. One day after application wheat plants are inoculated by spraying a spore suspension ($5 \times 10^5$ conidia/ml) on the test plants. After an incubation period of 1 day at 20° C. and 95% r.h. plants are kept for 10 days at 20° C. and 60% r.h. in a greenhouse. The disease incidence is assessed 11 days after inoculation.

Compounds of Tables 2, 3 and 4 show good activity in this test. The compounds 2.5, 2.17, 2.18, 2.23, 2.24, 2.33, 2.45, 2.46t, 2.76c, 2.76t, 2.77c, 2.77t, 3.5, 3.17, 3.23, 3.33, 3.39, 3.45, 3.76, 4.10 and 4.12 each exhibit strong efficacy (<20% infestation).

The invention claimed is:
1. 3-Difouromethyl-1-methyl-1H-pyrazole-4-carboxylic acid (2-bicyclopropyl-2-yl-phenyl)-amide having the formula:

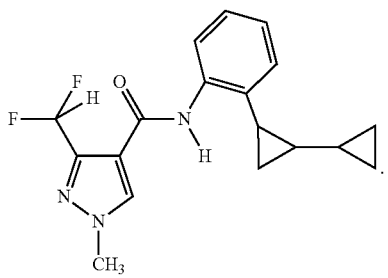

(I)

2. A composition for controlling microorganisms and preventing attack and infestation of plants therewith, wherein the active ingredient is a compound of formula (I) as claimed in claim 1 together with a suitable carrier.

3. A method of controlling or preventing infestation of cultivated plants by phytopathogenic microorganisms by application of a compound of formula (I) as claimed in claim 1 to plants, to parts thereof or the locus thereof.

* * * * *